(12) United States Patent
Merilainen et al.

(10) Patent No.: US 6,315,739 B1
(45) Date of Patent: Nov. 13, 2001

(54) APPARATUS AND METHOD FOR MEASURING THE INTRATRACHEAL PRESSURE OF AN INTUBATED PATIENT

(75) Inventors: Pekka Merilainen, Helsinki (FI); Ola Stenqvist, Göteborg (SE)

(73) Assignee: Instrumentarium Corporation

( * ) Notice: Subject to any disclaimer, the term of this patent is extended or adjusted under 35 U.S.C. 154(b) by 0 days.

(21) Appl. No.: 09/407,187

(22) Filed: Sep. 27, 1999

(51) Int. Cl.⁷ .............................. A61B 5/103; A61B 5/117
(52) U.S. Cl. .............................................................. 600/587
(58) Field of Search .................................. 600/587, 573, 600/561; 128/207.15, 200.26

(56) References Cited

U.S. PATENT DOCUMENTS

| | | | |
|---|---|---|---|
| 4,156,428 | * | 5/1979 | Henkin .............................. 128/207.15 |
| 4,716,896 | * | 1/1988 | Ackerman ........................ 128/200.26 |
| 4,813,431 | * | 3/1989 | Brown .................................... 600/561 |
| 5,088,332 | | 2/1992 | Merilainen et al. . |
| 5,235,973 | | 8/1993 | Levinson . |
| 5,752,921 | * | 5/1998 | Orr ........................................ 600/573 |
| 5,785,051 | * | 7/1998 | Lipscher et al. ................ 128/207.15 |

FOREIGN PATENT DOCUMENTS

| | | |
|---|---|---|
| 705 615 | 4/1996 | (EP) . |
| 2 521 013 | 8/1983 | (FR) . |

OTHER PUBLICATIONS

*Evaluation in Animals of a System to Estimate Tracheal Pressure from the Endotracheal Tube Cuff*, N. A. Wilder, et al., Journal of clinical Monitoring, 12: 11–16 (1996).

* cited by examiner

Primary Examiner—John P. Lacyk
Assistant Examiner—Brian Szmal
(74) Attorney, Agent, or Firm—Andrus, Sceales, Starke & Sawall, LLP

(57) ABSTRACT

An apparatus and method for determining the intratracheal pressure of a patient intubated with an endotracheal tube. An infusion conduit has a first end at the proximal end of the endotracheal tube and a second end proximate to the distal end of the endotracheal tube. The first end of the infusion conduit is connectable to a pressure sensing unit. A fluid source flows a gaseous or liquid fluid through the infusion conduit to maintain the patency of the infusion conduit from the first end to the second end and to allow the pressure obtained at the second end of the infusion conduit to be used to determine the intratracheal pressure of the subject.

30 Claims, 2 Drawing Sheets

APPARATUS AND METHOD FOR MEASURING THE INTRATRACHEAL PRESSURE OF AN INTUBATED PATIENT

BACKGROUND OF THE INVENTION

The present invention relates to an improved apparatus and method for measuring the intratracheal pressure of an intubated patient, and particularly, to such an apparatus and method suitable for use when an endotracheal tube is placed in the patient for a long period of time.

Patients undergoing post-operative or intensive care treatment are often mechanically ventilated through an endotracheal tube. An endotracheal or intubation tube is a flexible tube, typically formed of plastic. The tube is inserted through the mouth so that the distal end of the tube is located in the trachea and the proximal end extends out of the mouth of the patient. The distal end of the tube is retained in the trachea by an inflatable cuff surrounding the tube. The cuff can be filled with air by means of a syringe connected to an inflation passage at the proximal end of the tube.

A typical mechanical ventilator employed with an endotracheal tube has a breathing circuit comprising an inhalation limb and an exhalation limb connected to two arms of a Y-connector. The third arm of the Y-connector is connected, via a patient limb, to the proximal end of the endotracheal tube. The ventilator supplies breathing gases to the patient though the inhalation limb during inhalation. The contraction of the subject's lungs discharges breathing gases through the exhalation limb during exhalation. In addition to supplying breathing gases, the ventilator may be used to supply pharmaceutical agents for ventilation therapy by entraining the agents in the inhaled breathing gases.

Conditions in the breathing gas supply equipment and in the respiratory system of the patient are often monitored by one or more sensors connected along the flow path of the breathing gases to and/or from the patient. Parameters measured may include one or more of the concentration of a particular respiratory gas or gases, airway pressure, and airway volumetric gas flow. The pressure and flow characteristics or waveforms are particularly useful in deriving information regarding the lung mechanics of the patient. They may also be utilized to ascertain the presence of leaks and/or occlusions along breathing gas paths.

Prevailing medical opinion is currently of the view that, in the past, there has been a tendency to ventilate diseased lungs too aggressively in efforts to cure or alleviate the effects of lung disease. New guidelines have recently been introduced to provide direction in ventilating lungs in a manner now deemed preferable. These guidelines emphasize the importance of lung monitoring. Accurate parameter measurement is a vital aspect of effective lung monitoring.

The major variables of lung mechanics are the resistance to the passage of breathing gases and the compliance, or elasticity, of the patient's respiratory organs, primarily the lungs. The values of these parameters change during the course of serious lung disease and decisions to administer ventilation therapy, and the patient's response thereto, can be determined from the measured values.

In intubated patients, the resistance to the passage of breathing gases at the output of the ventilator comprises the resistance of the tracheobronchial tree of the patient in series with the resistance of the breathing gas pathway, including the endotracheal tube. This resistance is often called the total airway resistance. Since the flow through the series connected resistances is the same, when measuring gas flows, the flow sensor may be located proximally, distally, or at any desired location along the breathing gas flow path. However, the same is not true with respect to the measurement of gas pressures. In the measurement of gas pressures, it is important to measure the pressure as close to the alveoli of the lungs as possible. This is because the pressure drop along the endotracheal tube, caused by the respiratory gas flow, can be considerably greater in magnitude than the alveolar pressure. Thus, the standard practice of monitoring airway pressure at the proximal end of the endotracheal tube often gives misleading measurement data concerning the pressure conditions actually existing within the lungs of the patient. For example, a peak pressure of 40 cmH$_2$O may be measured at the proximal end of the endotracheal tube when, in fact, only 20 cm H$_2$O pressure exists in the lungs of the patient. This causes difficulties in calculating the resistance of the system and compliance of the lungs.

Also, the exhalation time of the patient may be too short to allow the lungs to empty completely of breathing gases. The pressure remaining in the patient's lungs, which may be characterized as an intrinsic positive end expiratory pressure, or PEEP, may remain undetected under current measurement techniques, due to the considerably higher pressure drop along the endotracheal tube. Either of these circumstances may lead to inaccurate evaluation of the condition or progress of the patient and to inappropriate therapeutic intervention.

For the foregoing, and other, reasons, it would be much more desirable to continuously monitor airway pressure at the distal end of the endotracheal tube so that the pressure drop of the endotracheal tube is eliminated and a more accurate measurement of intratracheal pressure is obtained.

In principle, it should be possible to measure the pressure at the distal end of the endotracheal tube, i.e. the intratracheal pressure, either directly by means of a sensor located at the distal end of the tube, or remotely via a pneumatic port at the distal end coupled to a remote sensor at the proximal end. However, the presence and movement of continuous secretions, such as mucus, of different and varying consistencies around the distal end of the endotracheal tube have heretofore made the, otherwise preferable, measurement of pressure at this intratracheal site difficult, particularly on a long term basis. Thus, while pressure sensors exist that are capable of measuring airway pressures on the order of 0–30 cmH$_2$O, the sensing element of such sensors needs to be covered by a protective, flexible cap. When the cap becomes covered by thick mucus or the like, the sensor may not be able to accurately indicate the magnitude of the intratracheal pressure. The same problem occurs with the use of a pneumatic channel or port which, when blocked by mucus or the like, is unable to transmit pressure conditions to a remote pressure sensor.

Because of the foregoing problems, techniques have been described to measure the pressure in the trachea indirectly using pressure measurements obtained from the inflated cuff of the endotracheal tube. See "Evaluation in Animals of a System to Estimate Tracheal Pressure from the Endotracheal Tube Cuff" by Wilder, Orr, and Westenskow in Journal of Clinical Monitoring 12:11–16, 1996.

BRIEF SUMMARY OF THE INVENTION

The object of the present invention is to provide an improved apparatus and method for measuring gas pressure at the distal end of an endotracheal tube inserted in the trachea of a patient by means of which the effects of secretions in the trachea on pressure measurement are avoided, even when the measurements are carried out over an extended period of time. The accurate, intratracheal pressure measurements so provided make available improved and safer lung monitoring and respiratory care or therapy to the patient.

Briefly, the apparatus and method of the present invention for determining a subject's intratracheal pressure employs an infusion conduit extending along an endotracheal tube positioned in the trachea of the subject. The infusion conduit has a first end located at the proximal end of the endotracheal tube and a second end proximate to the distal end of the endotracheal tube. A fluid source coupled to the first end of the infusion conduit flows a fluid through the infusion conduit to maintain the patency of the conduit. The column of fluid in the infusion conduit provides a pressure at the second end of the conduit that may be used to determine the intratracheal pressure of the patient. The fluid may comprise a gas, such as air or oxygen, or a liquid, such as water or saline solution. The infusion conduit may comprise a separate infusion tubing located in the lumen of the endotracheal tube. Or, the infusion conduit may be mounted in the peripheral wall of the endotracheal tube.

If the pressure at the proximal end of the endotracheal tube is also measured, the pressure difference between that obtained from the infusion conduit and that at the proximal end of the endotracheal tube may be used to determine conditions in the endotracheal tube, such as blockage by mucus secretions.

Various other features, objects, and advantages of the invention will be made apparent from the following detailed description and the drawings.

BRIEF DESCRIPTION OF THE SEVERAL VIEWS OF THE DRAWING

The invention will be further appreciated from the following detailed description, taken in conjunction with the drawing. In the drawing.

DETAILED DESCRIPTION OF THE INVENTION

Figure 1:
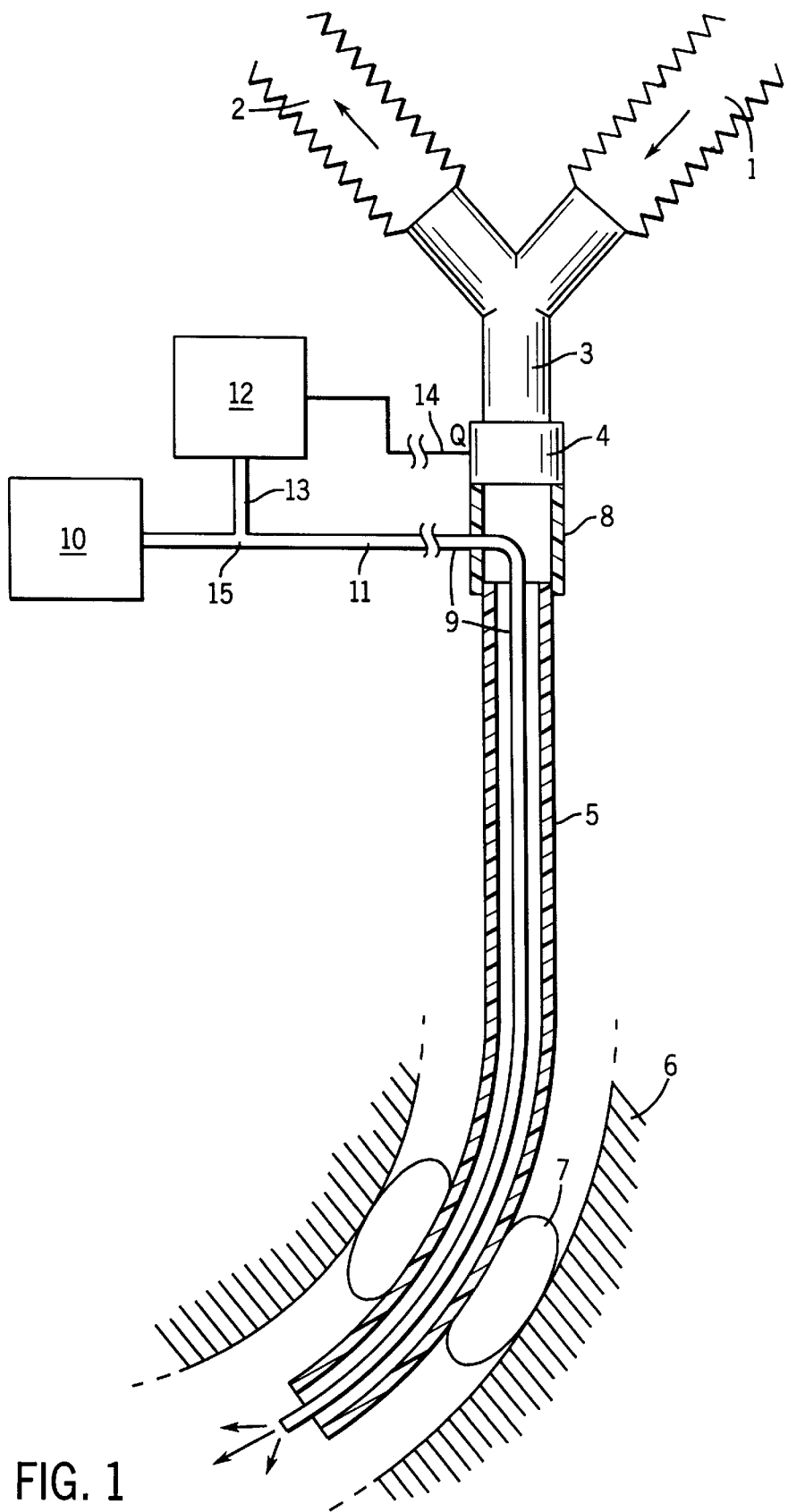
FIG. 1 is a somewhat schematic view of the intratracheal pressure measuring apparatus of the present invention along with associated patient ventilating equipment components.

In FIG. 1, inhalation limb 1 and exhalation limb 2 of a patient ventilator (not shown) are connected to two arms of Y-connector 3. Endotracheal tube 5 is coupled to the third arm of Y-connector 3 via sensor 4. Endotracheal tube 5 is inserted through the mouth of the patient so that the distal end of the tube is positioned in the trachea 6 of the patient. Tube 5 is sealed against the wall of the trachea and retained in the trachea with an inflatable cuff 7 in the conventional manner described above.

Sensor 4, which is typically interposed between Y-connector 3 and endotracheal tube 5, is responsive to the volumetric flow of the breathing gases to and from the patient. Airway flow sensor 4 may be of any suitable type, such as that shown in U.S. Pat. No. 5,088,332, assigned to the Instrumentarium Corp. The output Q of the flow sensor is provided to flow and pressure monitoring unit 12 as in line 14.

The apparatus of the present invention shown in FIG. 1 may be employed with adapter 8 interposed between flow sensor 4 and the proximal end of endotracheal tube 5. Adapter 8 may be integral with sensor 4 and/or endotracheal tube 5 or may be separate from either or both of these components. A pressure sensing conduit, which in the embodiment shown in FIG. 1 comprises a flexible tubing 9, passes through adapter 8 and along endotracheal tube 5 so that the distal tip of tubing 9 terminates at, or near, the distal end of endotracheal tube 5. For example, the distal tip of tubing 9 may terminate flush with the end of endotracheal tube 5 or plus or minus 1 cm from the end of tube 5. The proximal end of tubing 9 extends out of adapter 8. Flexible tubing 9 may have an inner diameter of 1.5 mm and typically will have an outer diameter of 3 mm.

The distal tip of tubing 9 is kept from being blocked by mucus or other secretions in the trachea of the patient by infusing a small, continuous flow of a fluid through tubing 9 and out the distal end of the tubing. For this purpose, fluid supply line 11 has one end connected to fluid source 10. The other end of fluid supply line 11 is connected to the proximal end of tubing 9. Line 11 is connected at point 15, intermediate its ends, by line 13 to a pressure sensor inside flow and pressure monitoring unit 12.

If the infusing fluid is a gas, source 10 may comprise a gas cylinder or the wall outlet of a hospital gas source. Typical gases that may be used in the present invention include air and oxygen. Liquid infusing fluids that may be used include water and saline solution. An elevated pouch may be used to supply distilled water or saline solution or an ordinary water supply may be used to supply tap water.

The infusion flow rate for gases is typically between 3 and 30 ml/min, and preferably around 10 ml/min, for a tubing 9 having the dimensions described above. The magnitude of the gas infusion flow rate is selected with a view toward minimizing the bias pressure caused by the product of the infusion gas flow and the flow resistance of tubing 9 between the connection point 15 in supply line 11 and the distal tip of tubing 9. At a flow of 10 ml/min a meter of tubing with an inner diameter of 1.5 mm has a pressure drop of about 1 cmH$_2$O. This is relatively small with respect to a typical peak pressure found in the trachea. To provide a direct reading of airway pressure, the bias pressure drop can be determined in a preliminary calibration procedure and set off against the pressure indication provided by flow and pressure monitoring unit 12.

When using a flow of liquid to keep tubing 9 open, the flow rate may be between 1 and 20 ml/hr the use of a small flow rate, such as 6 ml/hr, allows the liquid reaching the tip of tubing 9 to be evaporated by the body warmth inside the trachea. The moisture provided by the evaporation of a liquid, such as water, has a beneficial effect in keeping the trachea mucosa humid. The pressure drop along tubing 9 at such a low flow rate is negligible. When a liquid is used, the pressure monitoring portions of unit 12 connected to line 13 may be generally the liquid pressure sensing apparatus conventionally used in invasive blood pressure measurements.

In carrying out pressure measurements with the apparatus described above, the column of fluid flowing in tubing 9 and supply line 11 will transmit intratracheal pressures existing at the distal end of tubing 9 to flow and pressure monitoring unit 12 via line 13. As noted above, bias pressures due to infusing fluid flow resistance can be made small and can be offset during calibration. The continuous flow of fluid from the distal tip of tubing 9 prevents mucus or other secretions from blocking the transmission of the intratracheal pressures to monitoring unit 12.

Figure 2:
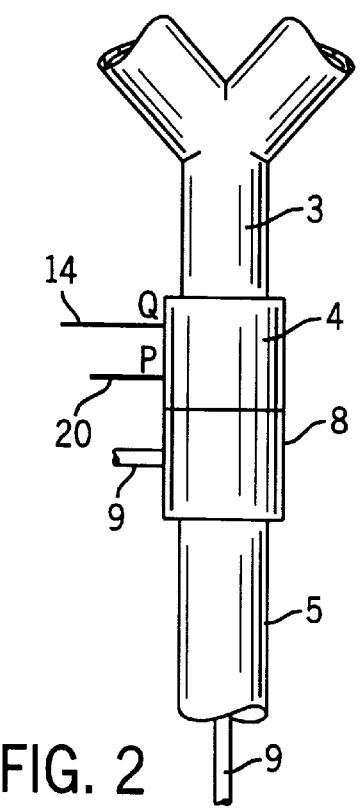
FIG. 2 shows a modification of the intratracheal pressure measuring apparatus of the present invention.

The pressure measurement provided by tubing 9 and the associated components at the distal ends of tubing 9 and tube 5 provides an additional advantage in that if a pressure measurement is also available at sensor 4, i.e. at the proximal end of endotracheal tube 5, changes in the resistance to breathing gas flow through endotracheal tube S can be determined. Increased resistance is usually an indication that the lumen of endotracheal tube 5 is becoming occluded by mucus or other secretion accumulations. A flow sensor 4 of the type shown in U.S. Pat. No. 5,088,332 employs the pressure drop across an obstruction to determine flow rates. Thus as shown in FIG. 2, a pressure indication P may be supplied from sensor 4 in line 20 to flow and pressure monitoring unit 12. Flow and pressure monitoring unit 12 determines the pressure difference between the distal end pressure obtained from tubing 9 in line 13 and the proximal end pressure obtained from line 20. Due to the infusion flow in tubing 9, the pressure measurement derived from tubing 9 will be largely unaffected by mucus accumulations. Should occlusion of the lumen of endotracheal tube 5 commence due to mucus accumulation or for other reasons, the pressure measured at sensor 4 will change because of the increased flow resistance along tube 5. The altered pressure difference between that obtained at the distal end of endotracheal tube 5 from tubing 9 and that measured at the proximal end of endotracheal tube 5 at sensor 4 is indicative of such a condition and possible need for cleaning endotracheal tube 5, as by suctioning.

Figure 3:
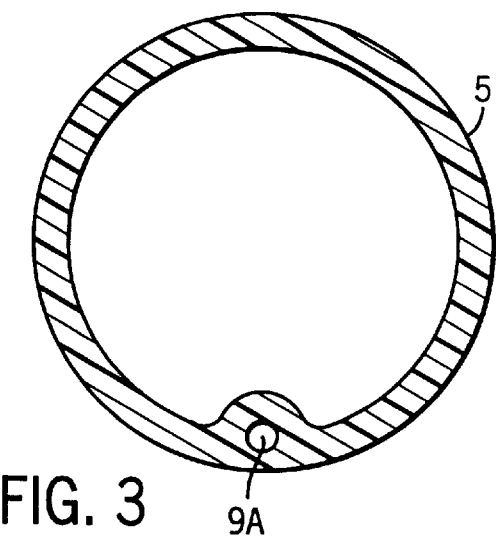
FIG. 3 is a cross sectional view showing another modification of the present invention.

While tubing 9 has been shown as a separate component placed in the lumen of endotracheal tube 5, it is also possible to integrate the conduit into the wall of the endotracheal tube. This is shown in FIG. 3 in which pressure sensing conduit 9A is shown as incorporated in the wall of endotracheal tube 5.

It is recognized that other equivalents, alternatives, and modifications aside from those expressly stated, are possible and within the scope of the appended claims.

What is claimed is:

1. Apparatus providing the intratracheal pressure of a subject existing at a distal end of an endotracheal tube, said endotracheal tube being positionable in the trachea of the subject with the distal end located in the trachea and a proximal end of the endotracheal tube adjacent the mouth of the subject, said apparatus comprising:

an infusion conduit having a first end and an open second end, said infusion conduit extending along the endotracheal tube to position said first end of said infusion conduit to exit from the proximal end of the endotracheal tube and to terminate the open second end of said infusion conduit at the distal end of the endotracheal tube and position the second end in proximity with the distal end of the endotracheal tube, the first end of said infusion conduit being connectable to a pressure sensing unit; and a fluid source coupled to the first end of said infusion conduit for flowing a fluid through said infusion conduit for discharge from said second end of said infusion conduit, said fluid source providing a fluid flow that maintains the patency of the infusion conduit and establishes and maintains a column of fluid in the infusion conduit that conveys the pressure existing at the second end of said infusion conduit to said first end of said infusion conduit to allow an indication of the pressure existing at the second end of the infusion conduit, and hence the intratracheal pressure of the subject, to be provided at the first end of said infusion conduit, the diameter of said infusion conduit being small as compared to that of the endotracheal tube yet sufficient to accurately convey the pressure at said second end to first second end of said infusion conduit.

2. The apparatus according to claim 1 wherein said fluid source is further defined as a gas source.

3. The apparatus according to claim 2 wherein said gas source flows a gas through said infusion conduit at a rate producing a desired pressure drop along said infusion conduit.

4. The apparatus according to claim 2 wherein said gas source flows gas through said infusion conduit in a flow range between 3 and 30 ml/min.

5. The apparatus according claim 4 wherein said gas flows gas through said infusion conduit at a rate of about 10 ml/min.

6. The apparatus according to claim 2 wherein gas source comprises a source of air or oxygen.

7. The apparatus according to claim 1 wherein said fluid source is further defined as a liquid source.

8. The apparatus according to claim 7 wherein said liquid source flows liquid through said infusion conduit in a quantity that is evaporated by the body heat in the trachea when discharged from said second end of said infusion conduit.

9. The apparatus according to claim 7 wherein said liquid source flows liquid through said infusion conduit at a rate between 1 and 20 ml/hr.

10. The apparatus according to claim 9 wherein said liquid source flows liquid through said infusion conduit at a rate of about 6 ml/hr.

11. The apparatus according to claim 7 wherein said liquid source comprises a source of water or saline solution.

12. The apparatus according to claim 1 wherein said infusion conduit extending along the endotracheal tube comprises an infusion tubing in the interior of the endotracheal tube.

13. The apparatus according to claim 1 wherein the endotracheal tube has a peripheral wall and wherein said infusion conduit is located in the peripheral wall of the endotracheal tube.

14. The apparatus according to claim 1 further including an adapter for said endotracheal tube by which endotracheal pressure determining apparatus may be mounted on the proximal end of said endotracheal tube.

15. The apparatus according to claim 1 wherein said infusion conduit is coupled to said fluid source by an infusion line extending between the infusion conduit and the fluid source and wherein said infusion line is connectable to a pressure measuring unit intermediate said fluid source and said first end of said infusion conduit.

16. The apparatus according to claim 1 further defined as apparatus for measuring the flow resistance of the endotracheal tube, said apparatus further comprising:

means for obtaining an indication of the gas pressure at the proximal end of the endotracheal tube; and means for determining the pressure difference between the pressure at the second end of said infusion conduit and the pressure at the proximal end of the endotracheal tube, said pressure difference indicating the flow resistance of the endotracheal tube.

17. The apparatus according to claim 1 wherein said apparatus includes, in combination, the endotracheal tube.

18. The apparatus according to claim 1 wherein said apparatus further includes measuring apparatus for determining the pressure existing at said second end of said infusion conduit.

19. A method for determining the intratracheal pressure of a subject existing at a distal end of an endotracheal tube, said endotracheal tube being positioned in the trachea of a subject with the distal end of the tube located in the trachea and a proximal end of the endotracheal tube adjacent the mouth of the subject, said method comprising the steps of:

providing an infusion conduit through the endotracheal tube with a first end of the conduit exiting from the proximal end of the endotracheal tube and an open second end of the infusion conduit opening in proximity to the distal end of the endotracheal tube;

flowing a fluid through the infusion conduit to render the infusion conduit patent and to establish and maintain a column of fluid in the infusion conduit that conveys the pressure existing at the second end of the infusion conduit to the first end of the infusion conduit; and obtaining an indication of the pressure existing at the second end of the infusion conduit as conveyed by the column of fluid to the first end of the infusion conduit to determine the intratracheal pressure of the subject.

20. The method according to claim 19 further defined as flowing a gas through the infusion conduit.

21. The method according to claim 20 further defined as flowing a gas through the infusion conduit at a rate producing a desired pressure drop along the infusion conduit.

22. The method according to claim 20 further defined as flowing gas through the infusion conduit in a flow range between 3 and 30 ml/min.

23. A method according to claim 22 further defined as flowing gas through the infusion conduit at a rate of about 10 ml/min.

24. The method according to claim 20 further defined as flowing a gas comprising air or oxygen through the infusion conduit.

25. The method according to claim 19 further defined as flowing liquid through the infusion conduit.

26. The method according to claim 25 further defined as flowing liquid through the infusion conduit in a quantity that is evaporated by the body heat in the trachea when discharged from the second end of the infusion conduit.

27. The method according to claim 25 further defined as flowing liquid through the infusion conduit at a rate between 1 and 20 ml/hr.

28. The method according to claim 27 further defined as flowing liquid through the infusion conduit at a rate of about 6 ml/hr.

29. The method according to claim 25 further defined as flowing a liquid comprising water or saline solution through the infusion conduit.

30. The method according to claim 19 further defined as a method for measuring the flow resistance of the endotracheal tube, said method further comprising the steps of obtaining an indication of the gas pressure at the proximal end of the endotracheal tube; and determining the pressure difference between the pressure at the second end of the infusion conduit and the pressure at the proximal end of the endotracheal tube, said pressure difference serving as a indication of the flow resistance of the endotracheal tube.

* * * * *